United States Patent [19]

Heady

[11] 4,335,207

[45] Jun. 15, 1982

[54] PROCESS FOR THE PRODUCTION OF HIGH FRUCTOSE SYRUPS AND ETHANOL

[75] Inventor: Robert E. Heady, Park Forest, Ill.

[73] Assignee: CPC International Inc., Englewood Cliffs, N.J.

[21] Appl. No.: 156,152

[22] Filed: Jun. 3, 1980

[51] Int. Cl.$^3$ .......................... C12P 7/14; C12P 19/02; C12P 19/04

[52] U.S. Cl. .......................................... 435/94; 435/97; 435/101; 435/105; 435/162; 435/813; 435/911; 435/940; 435/942

[58] Field of Search .................... 435/94, 97, 101, 105, 435/161, 162, 813, 911, 940, 942

[56] References Cited

U.S. PATENT DOCUMENTS 3,990,944  11/1976  Gauss et al. .......................... 435/165
4,077,842  3/1978  Cory .................................... 435/188
4,276,379  6/1980  Heady .................................. 435/94

FOREIGN PATENT DOCUMENTS 2000144  1/1979  United Kingdom .

OTHER PUBLICATIONS

Lodder, *The Yeasts,* North–Holland Publishing Co., Amsterdam, 575–579 (1970).
*The American Type Culture Collection Catalogue of Strain I,* 13th Ed, Rockville, Maryland, 354 (1978).

*Primary Examiner*—Esther M. Kepplinger
*Attorney, Agent, or Firm*—Stanley M. Parmerter

[57] ABSTRACT

This invention relates to a 2-step process for the preparation of fructose polymers and ethyl alcohol from sucrose. The fructose polymers are especially useful for the production of high fructose syrups.

14 Claims, No Drawings

PROCESS FOR THE PRODUCTION OF HIGH FRUCTOSE SYRUPS AND ETHANOL

FIELD OF THE INVENTION

This invention relates to a process for the production of fructose polymers and ethyl alcohol from sucrose. The fructose polymers produced can easily be converted to syrups of high fructose content.

BACKGROUND OF THE INVENTION

Commercial fructose-containing syrups are manufactured by the enzymatic isomerization of glucose obtained from corn-derived starch hydrolyzates. This is usually accomplished in a continuous process which involves contacting the glucose-containing solution with a glucose isomerase enzyme preparation that has been immobilized in some fashion. These procedures give a syrup in which fructose is less than 50%, usually 40-45%, of the total carbohydrate present.

Because fructose is sweeter than either glucose or sucrose, much effort has gone into developing processes for producing syrups in which more than 50% of the carbohydrate is fructose. Typically, these methods have involved chromatographic procedures for separating the fructose from the other carbohydrates contained in syrups derived from sucrose and/or corn. Examples are U.S. Pat. Nos. 4,096,036, 4,022,637 and 3,483,031.

Recently, a novel way to obtain fructose syrup of greater than 50% fructose content was disclosed in British Patent Specification No. 2,000,144. According to that procedure, a sucrose substrate is subjected to the action of a fructosyl transferase enzyme to convert the sucrose to an intermediate syrup containing predominantly fructose polymers and glucose. This syrup, in which the fructose is in polymeric form, is useful as a specialty carbohydrate or it can be further treated to produce fructose syrups of greater than 50% fructose content. About half of the glucose in the intermediate syrup can be isomerized to fructose by means of a glucose isomerase enzyme. Subsequent hydrolysis of this reaction mixture cleaves the fructose polymers to fructose, thereby producing a high fructose syrup containing a major amount of fructose and minor amounts of glucose.

SUMMARY OF THE INVENTION

In accordance with the present invention, there is provided a 2-step process for the production of ethyl alcohol and fructose polymers. The process involves contacting a sucrose-containing substrate with a fructosyl transferase enzyme. The resulting product is then fermented with a yeast preparation. Purification of the reaction product by removal of cellular debris (e.g., yeast cells) and ethanol yields a syrup containing fructose polymers. This syrup is useful as a specialty carbohydrate for sweetener and other applications. It may also be hydrolyzed to yield a syrup whose prinicipal sugar is fructose. The fructose content of the sugars in these syrups generally is higher than 66% (by weight) and ranges up to about 75% and even higher, depending upon the composition of the sucrose substrate and the reaction conditions employed.

An alternative embodiment of this invention involves contacting a sucrose-containing substrate with a mixture of fructosyl transferase and glucose isomerase enzymes. The resulting product is then fermented with a yeast preparation in a second step of the process. This alternative process produces ethyl alcohol and fructose polymers containing a very high percentage of fructose units. These fructose polymers may be hydrolyzed to yield a high fructose syrup containing over 80% fructose.

The process of this invention is a distinct improvement over prior processes for the preparation of fructose polymers. In this process, it is not necessary to separate the fructose polymer syrup from glucose which is formed concurrently. By fermenting the glucose in the secondary substrate with a yeast preparation that does not ferment the fructose polymers, separation of the glucose is obviated and a valuable, easily separated by-product, ethyl alcohol, is obtained.

DETAILED DESCRIPTION OF THE INVENTION

For purposes of this specification, the following definitions are provided for the various terms used herein:

1. Glucose and Dextrose

The terms "glucose" and "dextrose" are employed interchangeably in this application to embrace this monosaccharide in any form, in solution or dry.

2. Fructose and Levulose

The terms "fructose" and "levulose" are generally employed interchangeably in the art to refer to the isomer of dextrose that is sweeter than dextrose. Fructose is found in honey and in invert sugar, along with dextrose, and is valuable because of its sweetness. The terms levulose and fructose will be used interchangeably in this specification to refer to this monosaccharide in any form, in solution or dry.

3. High Fructose Syrup

This term as used herein refers to any syrup which contains more than 50% fructose by weight on a dry solids basis. It should be noted that commercial 42% fructose-bearing syrup is generally referred to as high fructose corn syrup, but is not intended to be included in the term as used herein.

4. Sucrose

The term "sucrose" refers to this disaccharide in refined or raw form, in solution or dry, from any sucrose raw material source, e.g., sugar cane or sugar beets. In the practice of this invention, the sucrose starting material is typically employed in aqueous medium.

5. Sucrose-Containing Substrate

The term "sucrose-containing substrate" is used herein to refer to any substrate in which sucrose is the predominant sugar. It includes molasses, turbinadoes, meladura, mixtures of sucrose and invert sugars, mixtures of sucrose and fructose-bearing syrup as well as purified sucrose.

6. Secondary Substrate

The term "secondary substrate" as used herein is the reaction product resulting from subjecting a sucrose-containing substrate to the action of a fructosyl transferase enzyme preparation, as defined herein.

7. Polysaccharide

The term "polysaccharide" is used herein to refer to any saccharide made up of two or more monosaccharide units.

8. Fructose Polymer

The term "fructose polymer" is used herein to refer to any polysaccharide in which the preponderance of monosaccharide units are fructose units.

9. Enzyme Preparation

The term "enzyme preparation" is used herein to refer to any composition of matter that exhibits the desired enzymatic activity. The term is used to refer, for example, to live whole cells, dry cells, cell extracts, refined and concentrated preparations derived from the cells and from culture liquors. The enzyme preparations may be used either in a solution or in an immobilized form in the practice of this invention.

10. Transfructosylation

This term as used herein refers to the transfer of a fructosyl group from a donor, e.g., sucrose, to an acceptor, e.g., polysaccharide.

11. Fructosyl Transferase Enzyme

As used herein, this term refers to any enzyme that catalyzes transfructosylation and includes the enzyme preparation derived from *Pullularia pullulans*, ATCC No. 9348 (synonymous with *Aureobasidium pullulans*). In its preferred embodiments, the fructosyl transferase enzyme preparation of this invention contains the fructosyl transferase enzyme in a purified form, that is, separated from the fermentation culture medium in which it was produced.

12. Fructosyl Transferase Unit

As used herein, one fructosyl transferase unit is defined as the amount of enzyme activity required to produce one micromole of reducing sugar, calculated as glucose, per minute under the following conditions: (a) pH 5.5, (b) temperature 55° C., and (c) substrate concentration at 60 g food-grade sucrose per 100 ml of an aqueous reaction mixture.

Reducing sugar (calculated as glucose) is determined using a "Technicon Autoanalyzer II" (Technicon, Inc., Tarrytown, N.Y.). Analysis is carried out by a conventional alkaline ferricyanide method, *Analytical Biochemistry* 45, No. 2, pp. 517–524 (1972), adapted for use in the "Autoanalyzer II". Unless otherwise designated, enzyme activity determinations are performed by continual monitoring of a reaction mixture consisting of the following composition:

7.5 ml. of 80% (w/v) aqueous food-grade sucrose solution.

2.3 ml 0.1 M citrate buffer pH 5.5.

0.2 ml enzyme sample containing that amount of fructosyl transferase enzyme which will produce from 5–25 micrograms of reducing sugar (calculated as glucose) per minute per ml of reaction mixture.

13. Glucose Isomerase Enzyme

Any enzyme preparation that isomerizes dextrose to levulose is referred to herein as a glucose isomerase enzyme. These enzymes are well known in the art and have been referred to as dextrose isomerase, xylose isomerase and glucose isomerase. Such enzymes can be derived from a variety of suitable microorganisms. Sources, purification, definition of units and methods of analysis of glucose isomerase enzymes are given in U.S. Pat. No. 4,077,842, which is incorporated herein by reference in its entirety.

14. Yeast Preparation

The term "yeast preparation" is used herein to refer to yeast cells capable of converting glucose to ethanol but which do not hydrolyze sucrose or fructose polymers to any significant degree. Absence of a hydrolyzing enzyme (an invertase) from the yeast preparation is important. If the polymers were hydrolyzed to give free fructose, the fructose would be destroyed by fermentation.

15. High Pressure Liquid Chromatographic Assay

This term as used herein defines a procedure whereby the syrups of the invention are analyzed using high pressure liquid chromatography in accordance with the following technique. Components are chromatographed by elution with water from a cation-exchange resin in the calcium form. Eluted components are detected by means of a differential refractometer. All carbohydrates are quantitated using an electronic integrator. The general procedure is that given in "Analysis of Carbohydrate Mixtures by Liquid Chromatography", *Am. Soc. Brew. Chem. Proc.*, 1973, pp. 43–46. The resin used is AMINEX 50W-X4 (20–30μ) in the calcuim form, Bio-Rad Laboratories, Richmond, Calif.

The sucrose-containing substrate used in this invention may be a solution of either refined or raw sucrose. The substrate may also be a mixture of sucrose and varying amounts of other sugars wherein the sucrose content is at least 50% by weight of the sugars present. Preferred substrates are commercial sources of sucrose such as molasses of varying degrees of purity or mixtures of sucrose with invert sugar. Other useful substrates include meladura, turbinadoes and mixtures of sucrose and fructose-bearing syrups. It is usually a question of economics as to which sucrose source is used. This will depend on the step or steps in the process where purification is most economically achieved.

The fructosyl transferase enzyme preparations preferred for use in this invention may be any enzyme preparations capable of transferring the fructose moiety of sucrose to another molecule of sucrose or to other sugar molecules so that the products are polysaccharides comprising from 2 to about 10 fructosyl units per molecule. Many such enzyme preparations are known. Excellent results have been obtained using the fructosyl transferase enzyme preparations derived from *Pullularia pullulans* such as NRRL No. 3937; ATCC No. 9348; ATCC No. 12535; NRRL No. 1673; NRRL No. Y 2311; NRRL No. YB 3892; ATCC No. 15223; and NRRL No. YB 3861. A procedure for the preparation of the fructosyl transferase enzyme from *Pullularia pullulans* is given in British Patent Specification No. 2,000,144, which is incorporated herein by reference in its entirety. An additional method for its preparation is given in Example 1.

The sucrose-containing substrate is treated with a fructosyl transferase enzyme to prepare secondary substrate in the first step of this process. The amount of fructosyl transferase enzyme used may vary widely. Practical rates of reaction are observed when from 10 to 30 fructosyl transferase enzyme units are used per gram of sucrose in the substrate.

Starting sucrose-containing substrate concentrations can range as low as 10 g per 100 ml of water. However, it is preferred to employ as high a dry substance concentration as possible, preferably ranging from about 30 g to about 60 g per 100 ml (for maximum reaction rate), up to the saturation point of sucrose.

The reaction to form secondary substrate may be carried out at any convenient temperature below that which inactivates the transferase enzyme. Preferably, the reaction temperature is from about 50° C. to about 60° C. The pH of the reaction mixture may vary from about 4.5 to about 6.5, and is preferably about 5.4 to 5.6 when the fructosyl transferase enzyme preparation is derived from a strain of *Pullularia pullulans*, ATCC No. 9348.

A secondary substrate, particularly useful for the preparation of a high fructose syrup, is prepared by the simultaneous action of fructosyl transferase enzyme and glucose isomerase enzyme preparations on a sucrose-containing substrate. In general, the concentrations of the sucrose-containing substrate, the temperature and pH of the reaction mixture, as well as the reaction time, are similar to those used when the sucrose-containing substrate is treated with a fructosyl transferase enzyme preparation alone. The principal difference is that in this case from about 10 to about 30 glucose isomerase enzyme units per gram of sucrose in the substrate were added. The pH at which the reaction with the two enzymes is carried out will vary with the nature of the enzymes used. When the glucose isomerase enzyme preparation employed is that obtained from *S. olivochromogenes*, ATCC No. 21715, a preferred pH of the reaction mixture is about 6.5.

The fermentation process of this invention is carried out using aqueous solutions of the substrate. Substrate concentrations from as low as about 10% (w/v) may be employed. However, it is preferred to use as concentrated solutions as practical, preferably ranging from about 30% to about 50% (w/v), so that there will be less need to evaporate water from the final product. The reactions are carried out at temperatures of from about 20° C. to about 35° C., preferably from about 24° C. to about 32° C., with the pH of the system from about 4.0 to about 6.5, but preferably from about 5.0 to about 5.5.

The yeast used to carry out the fermentation process of this invention may be any one capable of fermenting glucose to alcohol, but which does not hydrolyze fructose polymers or sucrose to any significant degree. As noted above, if the fructose polymers were hydrolyzed to free fructose, the fructose would be destroyed by fermentation. Ideally, the yeast strain most suited for this process will be osmophilic, alcohol tolerant, invertase free, lysis resistant, homofermentative and possess cell longevity. It can be a yeast with these characteristics found in nature or a yeast modified by mutation or genetic modification until it possesses the required characteristics. Any yeast of the genus Saccharomyces, which does not produce invertase enzymes, is generally useful. The yeast *Saccharomyces bailii*, ATCC No. 28166, is an example. The yeast *Saccharomyces cerevisiae*, ATCC No. 20598, is particularly suitable.

The concentration of yeast cells used to carry out the fermentation may vary over a wide range. However, it is convenient to employ about 1 g of wet cells for every 10 to 20 ml of 35% (w/v) substrate. Wet yeast cells obtained by centrifugation contain about 70–76% moisture. The yeast preparation used for the process of this invention may consist of yeast cells in either their growth or resting phase as long as they are capable of fermenting monosaccharides to ethyl alcohol.

Any conventional means, such as centrifugation or filtration, may be used to remove the yeast cells from the reaction mixture. Recovery of alcohol is most conveniently accomplished by distillation from the fermentation mixture. However, other means such as adsorption may be employed. For example, Ladisch, M. R. and Dyck, K. *Dehydration of Ethanol: New Approach Gives Positive Energy Balance*, In Science. 205: pp. 898–900. Aug. 31, 1979, which is hereby incorporated by reference in its entirety.

If high fructose syrup is desired as a product, the fructose polymers may be hydrolyzed. Hydrolyzing agents and conditions of hydrolysis must be chosen so that the fructose is not destroyed. The reaction may be catalyzed by an acid or an acidic resin. Alternatively, the hydrolysis may be accomplished by means of enzymes such as those contained in commercially available invertase enzyme preparations.

The following examples further describe the embodiments of this invention. All parts are by weight and all percentages are weight by volume (w/v) unless expressly stated to be otherwise.

EXAMPLE 1

Production of Fructosyl Transferase Enzyme

A. The Fermentation Procedure Used to Produce the Enzyme

The medium used for inoculum development and fermentation to produce the enzyme was as follows:
0.5% Dibasic Potassium Phosphate
0.1% Sodium Chloride
0.02% Magnesium Sulfate-Heptahydrate
0.6% Ammonium Sulfate
0.3% Yeast Extract (Difco Labs. Inc., Detroit, Mich.)
6.0% Sucrose (Food Grade)
pH of medium adjusted to 6.8.

A first-stage inoculum was prepared as follows. The seed flasks, 500-ml Erlenmeyers containing 100 ml of sterile medium, were inoculated from a slant culture of the black yeast, *Pullularia pullulans*. The particular strain of the yeast employed is designated in the catalogue of the American Type Culture Collection (Rockville, Md.) as ATCC No. 9348. The seed flasks, after development on a reciprocal shaker for 48 hours at 31° C., were used to prepare a second-stage inoculum. This was accomplished by placing 0.25-ml portions of the first-stage inoculum in 25 ml of medium in 250-ml Erlenmeyer flasks. The second-stage inoculum was developed on a reciprocal shaker for 24 hours at 31° C. The entire contents of one flask was used to inoculate a 7.5-liter fermentor containing 5 liters of the medium. The medium was identical with that used for the seed flasks except that the sucrose was at a 12% concentration rather than a 6% concentration, and 0.04% of polypropylene glycol, mol. wt. 2000, antifoam agent was added. The fermentations were carried out at 32° C., with an agitator speed of 500 rpm and with 4 liters of air per minute passing through the mixture. Fermentation was conducted for a total of 65 hours.

B. Recovery of the Enzyme from the Cells

The pH of the fermentor broth was adjusted to 5.5 with 4 N NaOH solution before it was run through a Sharples continuous centrifuge to separate the cells and cellular debris from the supernatant. The wet cells were placed in a 1-liter Erlenmeyer flask with 2 volumes of water. After the addition of 1% toluene and a small amount of Triton X-100 (an alkyl phenoxy polyethoxy ethanol, non-ionic detergent, manufactured by the Rohm & Haas Co., Philadelphia, Pa.), the flask was shaken for 1 hour on a reciprocal shaker to suspend the cells. The flasks were then left at room temperature for 3 days with occasional hand mixing. The mixture was filtered through a filter coated with diatomaceous earth, and the cells were washed with water. The filtrate was then concentrated by ultrafiltration through a Pellican Cassette System, manufactured by the Millipore Corp., Bedford, Mass., fitted with a cassette which retains material of greater than 10,000 molecular weight. During the concentration, the retentate was passed through reticulated foam before being returned to the ultrafiltration unit. The retentate was freeze-dried in a lyophilizer, ground in a mortar and pestle, washed with ethanol, and again lyophilized. The material from 6 such runs weighed a total of 39.9 g and showed an enzyme activity of 18,976 fructosyl transferase units per gram.

EXAMPLE 2

Preparation of Secondary Substrate

Food-grade sucrose, 4400 g, was dissolved in 4400 ml water. The pH of this solution was adjusted to 5.7 with dilute hydrochloric acid before dosing with 44,000 units of the fructosyl transferase enzyme from Example 1. The solution was incubated at 55° C. for 48 hours. The enzyme reaction was stopped by placing the container in a boiling water bath for 10 minutes. The resulting syrups were shown by analysis to contain 50.38% solids by weight. Carbohydrate composition was determined by high pressure liquid chromatography, with the following results:

| Carbohydrate Composition | |
| --- | --- |
| Fructose | 2.9% |
| Glucose | 32.9% |
| Sucrose | 8.2% |
| 1-Kestose | 17.9% |
| Nystose + Higher Polymers | 36.8% |

EXAMPLE 3

Culture of S. bailii Yeast

The medium used for inoculum development and fermentation to produce the cells was as follows:
1% Malt Extract
0.2% Ammonium Nitrate
0.2% Dibasic Potassium Phosphate
0.3% Yeast Extract (Difco Labs. Inc., Detroit, Mich.)
15% Secondary Substrate from Example 2
pH of medium adjusted to 5.5.

The seed flasks, 500-ml Erlenmeyers containing 100 ml of sterile medium, were inoculated from a slant culture of the yeast, *Saccharomyces bailii*. The particular strain of yeast employed was designated in the catalogue of the American Type Culture Collection (Rockville, Md.) as ATCC No. 28166. The seed flasks were shaken on a reciprocal shaker for 16 hours at 30° C. before the contents were pooled. To a 1-liter Erlenmeyer fermentation flask, containing 200 ml of the previously defined medium, was added 10 ml of the pooled inoculum. Two such flasks were developed on a reciprocal shaker for 24 hours at 30° C. before the contents were cooled. A 10-ml portion of this second inoculum was used to inoculate a 1-liter Erlenmeyer fermentation flask containing 200 ml of the following medium:
1.0% Malt Extract
0.2% Ammonium Nitrate
0.2% Dibasic Potassium Phosphate
0.3% Yeast Extract (Difco Labs. Inc., Detroit, Mich.)
5.0% Glucose
pH of medium adjusted to 5.5.

The fermentation was run at 30° C. on a reciprocal shaker for 24 hours before the broth was run through a Sharples continuous centrifuge to remove the cells. The wet cell pack from 40 such flasks weighed 84.4 g.

EXAMPLE 4

Fermentation of Secondary Substrate with S. bailii

To 844 ml of a 30% (w/v) solution of secondary substrate from Example 2, was added the 84.4 g of wet cells from Example 3. The pH was adjusted to 5.2 and maintained at this value with 0.5 N sodium hydrodixe solution while it was stirred for 22 hours at room temperature. The mixture was centrifuged to remove the yeast cells and the supernatant was analyzed by high pressure liquid chromatography with the following results:

| Carbohydrate Composition | |
| --- | --- |
| Glucose | 1.7% |
| Sucrose | 12.2% |
| 1-Kestose | 26.0% |
| Nystose + Higher Polymers | 58.9% |

Chromatographic analysis indicated that approximately 2% by volume of the supernatant was ethanol.

A portion of the filtrate was diluted with water to give a 10% (w/v) solution. This was then hydrolyzed with invertase (Pfanstiehl Laboratories, Waukegan, Ill.) using 0.1 ml of invertase per 10 ml of solution. The solution was covered with a few drops of toluene to inhibit microbial growth and incubated at 32° C. for 48 hours. Carbohydrate content of the resulting syrup, as determined by high pressure liquid chromatography, was found to be 68.0% fructose and 31.8% glucose.

These results demonstrate that by this process sucrose can be converted to high fructose syrup and ethyl alcohol with the production of minimum amounts of by-products.

EXAMPLE 5

Preparation of High Fructose Syrup and Ethanol from a Substrate Prepared by the Concurrent Action of Fructosyl Transferase and Glucose Isomerase Enzymes on Sucrose A. Preparation of Secondary Substrate Food-grade sucrose, 600 g, was dissolved in 600 ml of water. The pH was adjusted and maintained at 6.5 by the addition of 0.5 N sodium hyroxide solution as needed. To the sucrose solution was added 18,000 units of fructosyl transferase enzyme preparation, obtained by the method of Example 1 and 12,000 units of glucose isomerase enzyme prepared as described by Cory, U.S. Pat. No. 4,077,842. After the mixture had been stirred at 55° C. for 22 hours, it was heat treated to stop the enzyme reaction.

B. Fermentation of Secondary Substrate with *S.bailii*

To 540 g of the above solution was added sufficient water to dilute it to a volume of 1 liter. This gave a solution containing approximately 30% solids. To this solution was added 157 g of wet cells of *S. bailii* prepared as in Example 3. The pH of the mixture was adjusted and maintained at 5.2 by the addition of 0.5 N sodium hyroxide solution as needed. Stirring was continued for 22 hours at room temperature. The mixture was centrifuged to remove the yeast cells and the supernatant was treated with an invertase enzyme preparation as in Example 4. The resulting product was assayed by high pressure liquid chromatography for determination of carbohydrate composition with the following results:

| Carbohydrate Composition | |
| --- | --- |
| Fructose | 81.5% |

| Carbohydrate Composition | |
|---|---|
| Glucose | 18.4% |

A small sample of the supernatant separated from the yeast cells was shown by analysis to contain 3.9% ethyl alcohol by volume.

This example shows that a preferred substrate for the preparation of high fructose syrups by the method of this invention may be obtained by the concurrent action of a fructosyl transferase enzyme and a glucose isomerase enzyme on a sucrose-containing substrate.

EXAMPLE 6

Culture of *S. cerevisiae* Yeast

Strain 1453-3A was obtained from the Yeast Genetic Stock Center (Donner Laboratory, University of California, Berkeley, Calif. 94720). This strain is haploid, mating type a, suc (invertase-less), requires histidine and leucine for growth. It ferments maltose and melibiose. It is on deposit in the American Type Culture Collection (Rockville, Md.) as ATCC No. 20598.

The medium used for inoculum development and fermentation to produce the cells was as follows:

0.3% Yeast Extract
0.2% Malt Extract
0.5% Peptone
4% Maltose

The seed flasks, 500-ml Erlenmeyers containing 100 ml of sterile medium, were inoculated from a slant culture of the yeast. The seed flasks were shaken on a rotary shaker for 16 hours at 30° C. The cells were separated from the broth by means of a centrifuge. The combined wet cell pack from 5 such flasks weighed 7.3 g.

EXAMPLE 7

Fermentation of Secondary Substrate with *S. cerevisiae*

To 50 ml of a 35% (w/v) solution of a secondary substrate prepared as in Example 2 was added 5.0 g of wet cells from Example 6. The pH was adjusted to 5.5 by the addition of 0.05 g of calcium carbonate. The mixture was then stirred for 24 hours at room temperature. Centrifugation to remove yeast cells gave a clear supernatant that was analyzed by high pressure liquid chromatography with the following results:

| Carbohydrate Composition | |
|---|---|
| Fructose | 2.6% |
| Glucose | 0.6% |
| Sucrose | 13.0% |
| 1-Kestose | 22.1% |
| Nystose + Higher Polymers | 58.2% |

Chromatographic analysis indicated that 4.0% (w/v) of the supernatant was ethyl alcohol.

Treatment of the filtrate with an invertase enzyme preparation yielded a product which was assayed by high pressure liquid chromatography for the determination of carbohydrate composition with the following results:

| Carbohydrate Composition | |
|---|---|
| Fructose | 71.6% |
| Glucose | 28.0% |

A fermentation run under the same conditions, except that 5.0 g of the yeast cells from *S. bailii* (Example 3) was used, yielded a high fructose syrup whose carbohydrate composition was 71.3% fructose and 28.5% glucose. In this case, the supernatant contained only 2.0% (w/v) of ethyl alcohol.

The foregoing experiments demonstrate that the novel process of this invention is a convenient method for preparing high fructose syrups. The intermediate secondary substrate containing fructose polymers need not be isolated. Rather, it may be converted in situ to a high fructose syrup plus a valuable, easily separated by-product, ethyl alcohol.

What is claimed is:

1. A process for the production of ethyl alcohol and fructose polymers comprising the sequential steps of contacting a sucrose-containing substrate with an effective amount of a fructosyl transferase enzyme to produce a secondary substrate followed by fermenting said secondary substrate with an effective amount of a yeast preparation, that does not hydrolyze sucrose or fructose polymers or ferment fructose polymers, to ferment the glucose in the secondary substrate to alcohol.

2. The process of claim 1 wherein said yeast preparation is a Saccharomyces, said substrate is sucrose and said fructosyl transferase enzyme preparation is obtained from *Pullularia pullulans*.

3. The process of claim 2 wherein said fructosyl transferase enzyme preparation is derived from *Pullularia pullulans*, ATCC No. 9348.

4. The process of claim 3 wherein said yeast preparation is *Saccharomyces bailii*, ATCC No. 28166, and the reaction is carried out at a temperature of from about 24° C. to about 32° C. and at a pH of from about 5.0 to about 5.5.

5. The process of claim 3 wherein said yeast preparation is *Saccharomyces cerevisiae*, ATCC No. 20598, and the reaction is carried out at a temperature of from about 24° C. to about 32° C. and at a pH of from about 5.0 to about 5.5.

6. The process of claim 1 wherein said fructosyl transferase enzyme preparation is derived from *Pullularia pullulans*, ATCC No. 9348, and said yeast is *Saccharomyces bailii*, ATCC No. 28166, and the reaction is carried out at a temperature of from about 24° C. to about 32° C. and at a pH of about 5.0 to 5.5.

7. The process of claim 1 wherein said yeast is *Saccharomyces cerevisiae*, ATCC No. 20598, and the reaction is carried out at a temperature of from about 24° C. to about 32° C. and at a pH of about 5.0 to about 5.5.

8. The process of claim 1 wherein the sucrose-containing substrate is contacted with a mixture of a fructosyl transferase enzyme and a glucose isomerase enzyme to produce a secondary substrate.

9. A process for the production of a high fructose syrup and ethyl alcohol which comprises:
   (a) contacting a sucrose-containing substrate with an effective amount of a fructosyl transferase enzyme to produce a secondary substrate;
   (b) fermenting the secondary substrate with an effective amount of a yeast preparation, that does not hydrolyze sucrose or fructose polymers or ferment fructose polymers, to ferment the glucose in the secondary substrate to alcohol; and (c) treating the resulting mixture with a reagent capable of hydrolyzing polysaccharides to monosaccharides to give a high fructose syrup.

10. The process of claim 9 wherein said fructosyl transferase enzyme preparation is derived from *Pullularia pullulans*, ATCC No. 9348.

11. The process of claim 9 wherein the yeast is any Saccharomyces which is essentially free of invertase activity.

12. The process of claim 11 wherein the yeast is *Saccharomyces bailii*, ATCC No. 28166, and the reaction is carried out at a temperature of from about 24° C. to about 32° C. and at a pH of from about 5.0 to about 5.5.

13. The process of claim 11 wherein the yeast is *Saccharomyces cerevisiae*, ATCC No. 20598, and the reaction is carried out at a temperature of from about 24° C. to about 32° C. and at a pH of from about 5.0 to about 5.5.

14. The process of claim 9 wherein the sucrose-containing substrate is contacted with a mixture of a fructosyl transferase enzyme and a glucose isomerase enzyme to produce the secondary substrate.